United States Patent
Nevo et al.

(10) Patent No.: US 6,174,283 B1
(45) Date of Patent: *Jan. 16, 2001

(54) APPARATUS AND METHOD FOR MONITORING A SYSTEM AND DISPLAYING THE STATUS OF THE SYSTEM

(75) Inventors: Igal Nevo, Bala Cynwyd; Maher Salah, Philadelphia; Srinivas S. Dagalur, Philadelphia; Mark Newman, Philadelphia, all of PA (US)

(73) Assignee: Albert Einstein Healthcare Network, Philadelphia, PA (US)

( * ) Notice: Under 35 U.S.C. 154(b), the term of this patent shall be extended for 0 days.

This patent is subject to a terminal disclaimer.

(21) Appl. No.: 08/734,332

(22) Filed: Oct. 21, 1996

Related U.S. Application Data

(63) Continuation-in-part of application No. 08/647,396, filed on May 9, 1996, now Pat. No. 5,772,599.

(51) Int. Cl.⁷ .................................................. A61B 05/00
(52) U.S. Cl. .......................... 600/301; 600/483; 600/484; 600/513
(58) Field of Search ..................................... 600/481, 483, 600/484, 513, 529, 531, 544, 545, 301

(56) References Cited

U.S. PATENT DOCUMENTS

| | | |
|---|---|---|
| 4,796,639 | 1/1989 | Snow et al. . |
| 4,834,107 | 5/1989 | Warner . |
| 5,355,889 * | 10/1994 | Nevo et al. .......................... 600/483 |
| 5,464,012 * | 11/1995 | Falcone ................................ 600/481 |
| 5,772,599 * | 6/1998 | Nevo et al. .......................... 600/483 |

OTHER PUBLICATIONS

Moulder et al., "Afrequency–time domain signal processing system", Medical Instrumentation, vol. 14, No. 2, 1980.*

Nevo, Igal & Salah, Maher Dislay Content For Operation Room and Intensive Care Unit, The 14th International Symposium on Computing in Anesthesia and Intensive Care, Apr. 1994, Rotterdam Holland.

Nevo, I., Roth, J.V., Ahmed, F. & Guez, A. Vital Function Status: A Parameter to Facilitate Decision Making in Anesthesia, J. Clin. Mon. 7:1, Jan., 1991, pp. 124–125.

Scheke, Th., Rau, G., Popp, H.J., Kasmacher, H. Kalff, G. Zimmermann & H.J. A Knowledge–Based Approach to Intelligent Alarms in Anesthesia, IEEE Engineering in Medicine and Biology, Dec. 1991, pp. 38–44.

Guez, A. & Nevo, I. Neural Networks and Fuzzy Logic in Clinical Laboratory Computing with Application to Integrated Monitoring, Clinica Chimica Acta 248 1996, pp. 73–90.

Nevo, I., Guez, A., Ahmed, F. & Roth, J.V. System Theoretic Approach to Medical Diagnosis, Computer–Based Medical Systems: Fourth Annual IEEE Symposium, 1991, pp. 94–96.

(List continued on next page.)

Primary Examiner—Robert L. Nasser
(74) Attorney, Agent, or Firm—John S. Childs, Jr.

(57) ABSTRACT

An apparatus and method for monitoring a system or patient to provide information regarding the status of the system. The apparatus comprises a means of transforming measured values of more than one parameter of the system using a function dependent on at least baseline and critical values of the parameters. The apparatus further includes mapping means for mapping the function to a sequence of reference values and generating a deviation indicator for each parameter. The deviation indicators are analyzed by an analyzer to generate information concerning the status of the system or patient.

38 Claims, 9 Drawing Sheets

OTHER PUBLICATIONS van der Aa, J., Beneken, J., van Oostrom, & J.H. & Gravenstein, J.S., Intraoperative Information Transfer: A Summary Display of Patient Status, J. Clin. Mon. 8:2, 1992, pp. 153–154.

Nevo et al., A New Patient's Status Indicator to Facilitate Decision Making In Anesthesia, Computer–Based Medical Systems, Fourth Annual IEEE Symposium, 1991, pp. 88–93.

Matsiras, P.V., PONI: An Intelligent Alarm System for Respiratory and Circulatory Management in the Operating Rooms, Jun. 1989, pp. 123–137.

van der Aa et al., J. Integration Concepts for Anesthesia Workstation Displays, J. Clin. Mon. 8:2, 1992, pp. 151–152.

Ahmed et al., Anesthesioligist's Adaptive Asscoiate, IEEE–EMBS, Philadelphia, 1990, pp. 49–50.

Nevo et al., Vital Function Status—A Parameter to Facilitate Decision Making in Anesthesia, Orlando, 1991.

* cited by examiner

APPARATUS AND METHOD FOR MONITORING A SYSTEM AND DISPLAYING THE STATUS OF THE SYSTEM

This application is a continuation-in-part of application Ser. No. 08/647,396, entitled "Apparatus and Method for Monitoring a System", filed May 9, 1996, now U.S. Pat. No. 5,772,599 which is incorporated herein by reference.

FIELD OF THE INVENTION

The present invention relates to an apparatus and a method for monitoring a system and, more specifically, to an apparatus and a method for monitoring a system to provide information regarding the status of the system.

BACKGROUND OF THE INVENTION

Many industries require that vast amounts of data pertaining to a particular system be monitored and analyzed in order to make split-second assessments concerning the condition of the system. For example, physicians and anesthesiologists routinely monitor more than thirty physiological parameters (e.g., heart rate, blood pressure, cardiac output, etc.) when treating patients in intensive care units, operating rooms, and emergency rooms. Also, financial advisors and analysts in the course of their work frequently check many parameters that can influence stock prices (e.g., closing price, 52-week high and low, dividends, yield, change, previous day high and low, etc.) in order to appropriately advise their clients. Further, control room operators, such as in industrial, power plant, and aviation control rooms, monitor a variety of outputs to insure that the system being monitored is functioning properly.

Often, misdiagnosis of the condition of the system occurs because of the sheer volume of the data to be monitored. For example, in the field of anesthesiology, anesthesiologists are surrounded by multiple vital sign monitors that display many data elements and can generate a myriad of alarms. In the noisy and congested atmosphere surrounding an operation on a patient or in the initial period after the operation when a large number of patients may be monitored by a few persons, busy physicians and nurses can miss physiological changes in the patient that are material to the well being of the patient. In this regard, it is estimated that in the United States, between 2,000 and 10,000 patients die each year from anesthesia related accidents. It is believed that many of these accidents could be avoided by transforming the plethora of data currently provided to the physician by monitors into a more useful form that would provide an earlier indication of physiological changes in the condition of the patient.

Monitoring systems have been developed to assist users in processing vast amounts of data. For example, in the medical profession, a patient monitoring system has been described wherein a plurality of medical parameters are measured and transformed to provide a danger level associated with each parameter. The highest danger level is selected to represent the status of the system. The transformation of the medical parameters is performed using a function exhibiting a maximum slope for parameter values near the homeostasis level for that parameter. As the system is extremely sensitive to small changes in each parameter about the homeostasis level of each parameter, the system can lead to false warnings. Also, the measurement of the highest danger level can have limited usefulness as an indicator of the status of the system or patient. More frequently, the user can better assess the status of the system or patient if the user is provided with information about the parameters not registering the highest danger or critical level and information about the parameter at the highest danger or critical level before that parameter reached the critical level.

In light of the above, it would be advantageous to provide an apparatus and method for monitoring a system wherein an overwhelmingly large amount of data is consolidated to provide the user with a manageable amount of information to assess the condition of the system and changes in most, if not all, of a set of measured parameters associated with the system. Preferably, the apparatus and method is responsive to the requirements of the user and the specific system being monitored. In addition, the system and method should minimize the number of false warnings and be rapid enough to provide information in a time frame that is required by the user.

SUMMARY OF THE INVENTION

The disadvantages associated with the known apparatus and methods for monitoring systems are overcome by an apparatus and method in accordance with the present invention. According to the present invention, individual measured parameters are transformed to generate one or more status indicators. The status indicators provide a user with valuable information for assessing the overall status of the system. In addition, the status indicators can be calculated on-line, in real-time, thereby providing the user with up-to-date information so that the user may quickly respond to problems as they arise. Further, the transformation may be dependent upon individual characteristics of both the particular user and the particular system being monitored. Accordingly, the user will have an intuitive, as well as an empirical, understanding of how decisions regarding the system will influence the transformation of the system.

An apparatus according to the present invention optionally comprises physical sensors or logical sensors, such as monitors, for measuring the values of a plurality of parameters associated with the system of interest. The specific number and types of sensors used will depend upon the particular system being monitored. In one embodiment, the sensors are small enough to be directly attached to the system. An example of such a sensor is a temperature probe. Additionally, the sensor may be a component of a remote sensing station. Accordingly, the sensor can supply measured values to the remote sensing station in either a continuous mode or on demand. Further, the sensor or the remote sensing station may be provided with a data storage means, such as a computer readable disk, for storing the values measured by the sensor so that the values can be processed at a later time.

The sensors are connected to or incorporate a processor so that the values of the measured parameters are passed from the sensors to the processor across one or more signal lines. The processor comprises a transformer which transforms the measured value of each parameter to a deviation indicator. The transformer preferably utilizes three parameter-dependent coefficients, such as baseline, minimum, and maximum values, to generate the deviation indicator corresponding to each parameter. The parameter-dependent coefficients are preferably transferred to the transformer from a user interface, such as a computer keyboard, or from a data-storage means, such as a computer readable disk. The user interface communicates with the transformer via signal lines.

The deviation indicators corresponding to each parameter are then passed to an analyzer across another signal line. The analyzer analyzes or evaluates the individual deviation indicators and generates one or more status indicators. The status indicators represent information regarding the overall status of the system being monitored. This information can be provided to the user so that the user can assess the status of the system. Additionally, the status indicators can provide the user with information regarding the status of individual deviations of certain parameters comprising a subsystem of the system. Preferably, the status indicators comprise a maximum deviation indicator, an average deviation indicator, and/or a system criticality indicator.

The deviation indicators are then displayed in a form that is easily analyzed by the user. In a preferred embodiment, the deviation indicators are displayed by providing a pictorial representation of the general system showing at least one structure associated with one or more of the measured parameters and labels identifying the parameters, subsystems and/or sensors. The labels comprise descriptors which inform the user of the parameters, subsystems and/or sensors being identified by the labels. The labels also comprise display windows for displaying of the deviation indicator associated with the parameters, subsystems and/or sensors. The degree of deviation of the deviation indicator is preferably indicated by assigning different colors to different degrees of deviation and displaying the indicator in the appropriate color. An up or down arrow can also be displayed to indicate whether the measured value of the parameter system and/or sensor has shifted above or below the baseline value for that parameter system and/or sensor. The display window also preferably displays on an ongoing basis the specific measured data for the parameter.

The present invention also relates to a method for monitoring a system. In the method according to the present invention, a user generates a system profile. The system profile contains system-specific and user-specific information corresponding to each of a plurality of parameters associated with the system being monitored. Preferably the information indicates the baseline, minimum, and maximum values for each parameter.

The values of each parameter are then measured. Each measured value is transformed to provide a deviation indicator for each parameter. The deviation indicator reflects the severity of the deviation of the measured value from the baseline value. Preferably, the deviation indicator is an integer value between zero and five, with higher values indicating a more severe deviation.

The deviation indicators are analyzed in order to generate one or more status indicators. The status indicators provide information on the system or one or more subsystems concerning the overall status or changes in the status over time. Preferably, the status indicators inform the user about the maximum deviation, the average deviation, and/or the system criticality.

Finally, the status indicators are presented to the user in a form which conveys to the user the status of the system. Based on the status indicators, the user can take appropriate action to either improve the status of the system or maintain the current status of the system.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
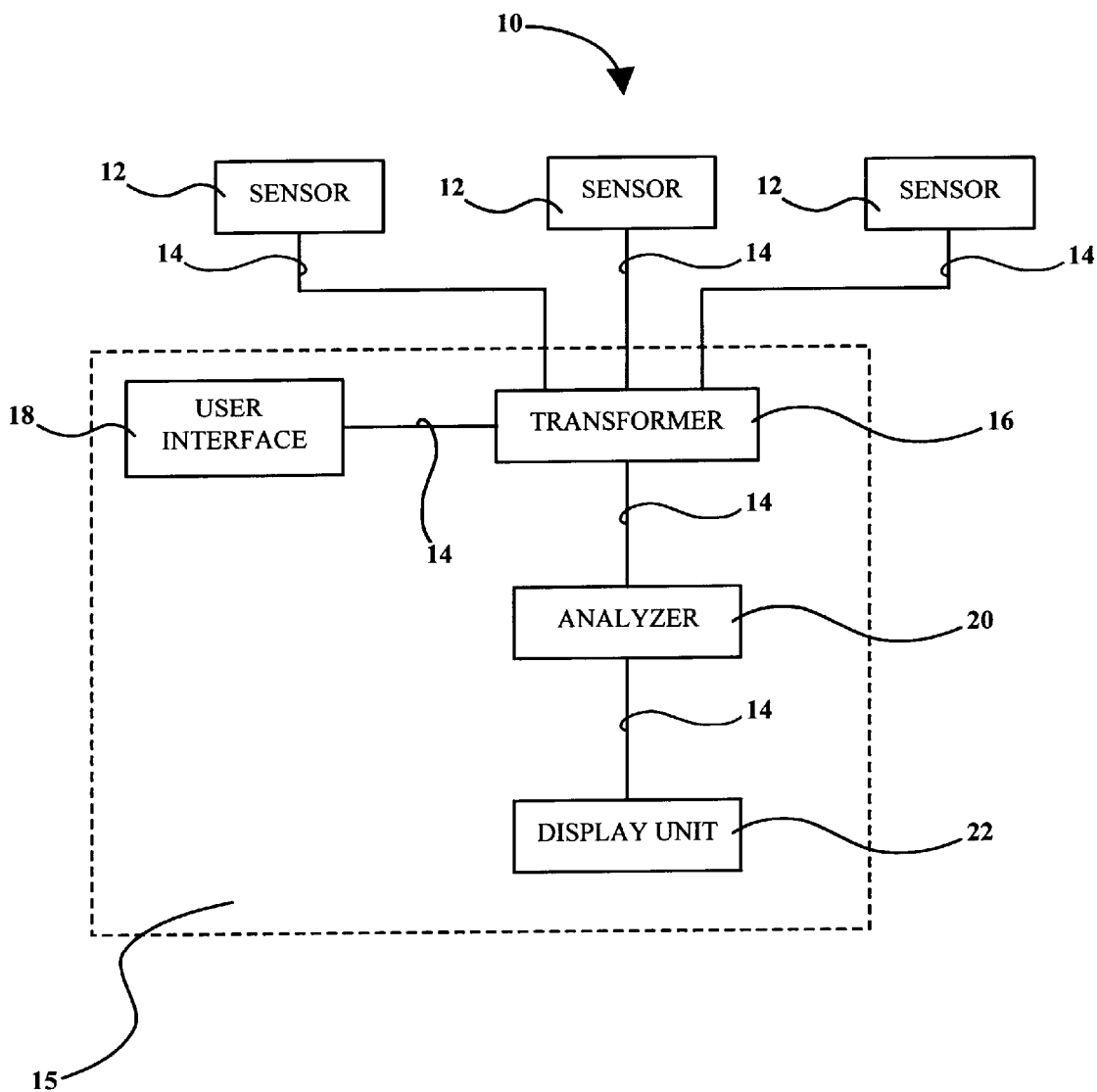
FIG. 1 is a schematic representation of an apparatus for monitoring a system in accordance with the present invention.

An apparatus 10 for monitoring a system in accordance with the present invention is shown schematically in FIG. 1. The apparatus 10 comprises three sensors 12 operatively connected to the system for measuring the values of three separate parameters associated with the system. However, the number and types of sensors 12 used will vary, depending upon the specific application. For example, when the status of a patient is being monitored in an operating room or intensive care setting, more than thirty different physiological parameters (e.g., heart rate, blood pressure, cardiac output, etc.) are typically measured.

The measured values of the parameters are then transferred from a sensor to a processor 15 across one or more signal lines 14. In one embodiment, the sensors 12 are interfaced to the processor 15 using an RS-232 serial multiplexer. The processor 15 can comprise a single stand-alone unit or it can be linked to a departmental network using client/server architecture. In one embodiment, the processor 15 comprises a PC Pentium platform using UNIX or Windows NT operating system. Further, the processor 15 is developed as an object oriented implementation in the C++ language. The processor 15 uses an Ethernet Network card and runs TCP/IP communication protocol. Cables or wireless communication devices may be used by the network architecture.

The processor 15 optionally comprises a user interface 18 for transferring a system profile to a transformer 16 across a signal line 14. Preferably, the user interface 18 is in the form of a computer keyboard so that the user can directly input information to the transformer 16. Accordingly, the user interface 18 can be developed using an OSF/MOTIF Toolkit. Alternatively, the system profile can be stored in a form which can be accessed by the transformer 16. The system profile supplied to the transformer 16 comprises information about the baseline, minimum, and maximum values of each of the parameters. Identifying information about the system (i.e., system type, user's name, identification number, time, date, etc.) can also be provided.

The transformer 16 takes the measured values of each parameter and generates a deviation indicator for each parameter. The transformer 16 assigns to each parameter a deviation indicator which represents the level of danger associated with the parameter. In one embodiment, each parameter is assigned one of six levels of danger, ranging from zero to five according to the following scale:

0 = baseline, no deviation
1 = minimum deviation
2 = mild deviation
3 = moderate deviation
4 = severe deviation
5 = very severe deviation Accordingly, the transformation maps each parameter into numbers representing the state of each parameter relative to the system's homeostatic conditions (i.e., baseline values for each parameter) and to prescribed maximum and minimum reference values for each parameter.

The individual deviation indicators are then transferred across a signal line 14 to an analyzer 20. The analyzer 20 analyzes or evaluates the values of the deviation indicators and generates one or more status indicators. The status indicators contain information regarding the overall status of the system. In one embodiment, the analyzer 20 analyzes the individual deviation indicators to each other to determine the maximum deviation indicator, the average indicator, and/or the system criticality.

A display unit 22 is provided for communicating the status indicators to the user. The display unit 22 is connected to the analyzer 20 by a signal line 14 which allows the status indicators to be passed from the analyzer 20 to the display unit 22. Preferably, the display unit 22 comprises a video monitor so that the status indicators can be visually displayed in a form that is easily analyzed by the user.

Figure 2:
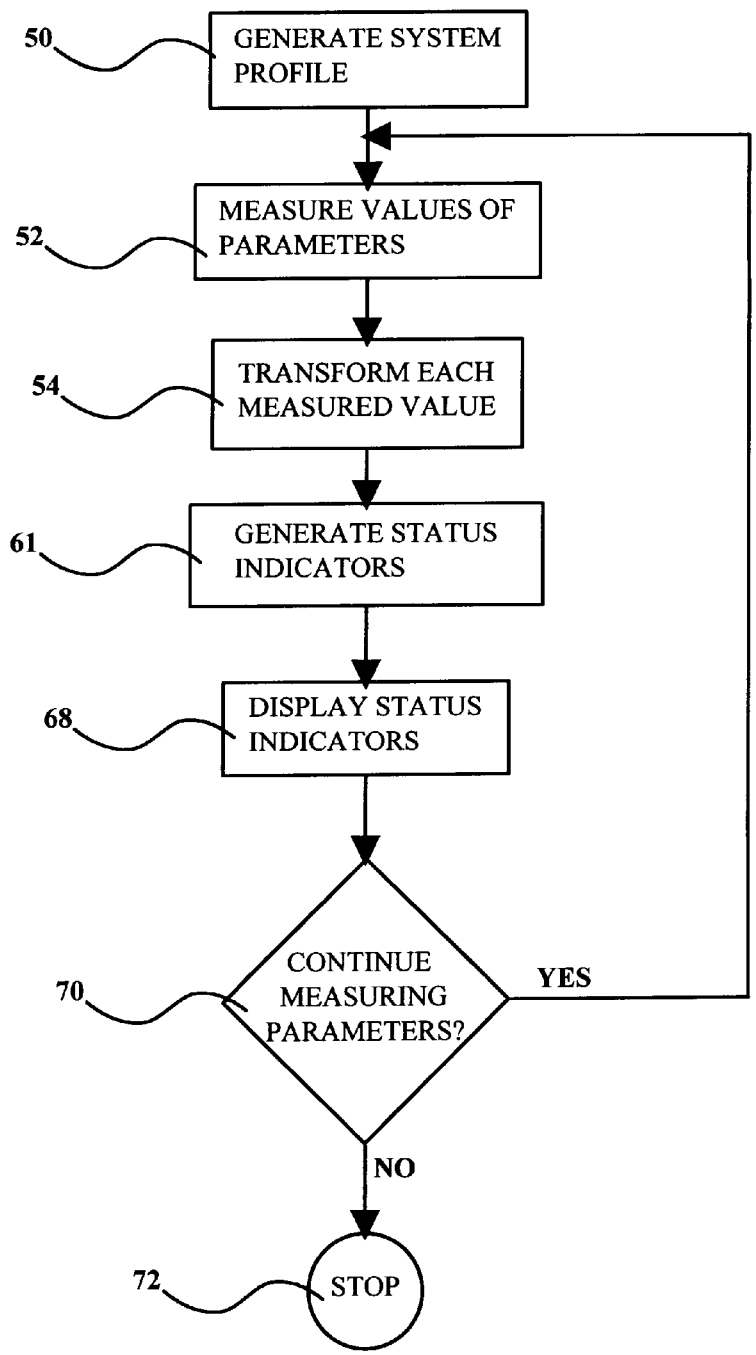
FIG. 2 is a flow chart showing the steps involved in a method for monitoring a system in accordance with the present invention.

The present invention also relates to a method, such as a computer-controlled method, for monitoring a system as depicted in FIG. 2. According to the method, a system profile is generated at step 50. The user is given an option of either creating a new system profile or recalling an old one. If a new system profile is to be created, the user inputs information regarding the parameters to be monitored. For most applications, such information includes the number and types of parameters to be monitored and a baseline, a minimum, and a maximum value for each parameter. If, however, an old system profile is to be used, the user is preferably given an option to adjust the existing system profile. Accordingly, the user may change the number and/or types of parameters to be monitored or alter the baseline, minimum, or maximum values associated with the parameters.

The system profile may be generated by inputting information into the system 10 with a user interface 18, such as a computer keyboard. For most applications, the minimum and maximum values for the parameters will be the same for similar types of systems. However, the baseline values are likely to differ from system to system, even for similar systems. Accordingly, the method of the present invention allows the user to tailor the system profile to the individual characteristics of the system to be monitored.

Once the system profile has been generated, the values of the individual parameters are measured at step 52. The number of parameters that should be measured will vary from system to system and application to application. However, the method of the present invention is completely applicable to the measurement of any number of parameters.

At step 54, the measured value of each parameter is transformed to yield a deviation indicator for each parameter. Preferably, the measured values are mapped into a corresponding deviation indicator using a transformation function which has a minimum sensitivity for deviations close to the baseline value of the parameter. Also, the function is preferably asymmetric about the baseline value to provide the user with greater flexibility. Toward that end, the function reflects the information regarding the parameters which was generated as part of the system profile at step 50.

Figure 3:
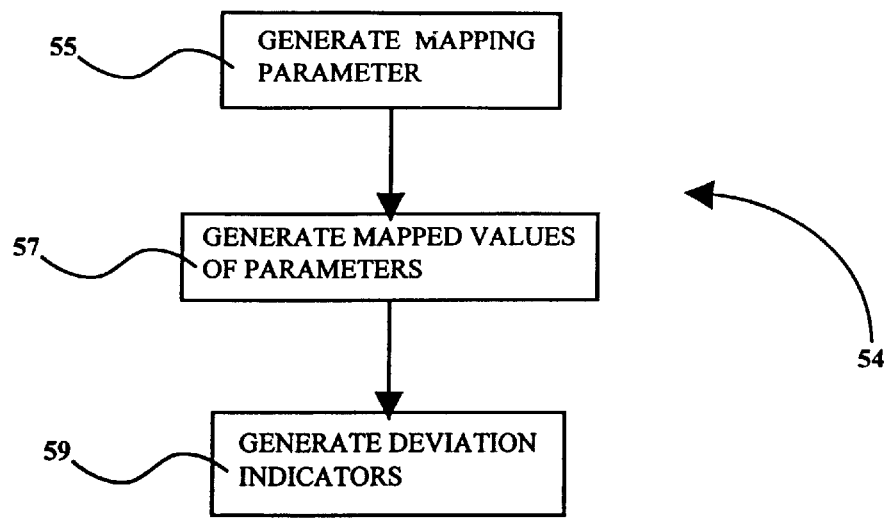
FIG. 3 is a flow chart showing the steps involved in a transformation step of FIG. 2.

The process for transforming each measured value into a deviation indicator at step 54 is shown in greater detail in FIG. 3. A mapping parameter is generated for each parameter at step 55. The form of the mapping parameter is determined by the function used to effectuate the transformation. The mapping parameter reflects the information regarding each parameter which was generated as part of the system profile at step 50. Preferably, the mapping parameter is different for values of the parameter above the baseline value and below the baseline value.

Once the value of the mapping parameter has been determined, the mapped value of the parameter is generated at step 57. The mapped value is generated using the transformation function and the appropriate value for the mapping parameter.

The mapped value of each parameter is then used to generate the deviation indicator for each parameter at step 59. The deviation indicator is determined by assigning to each parameter a level of danger associated with the parameter. Preferably, the higher the mapped value, the higher the level of danger. In one embodiment, each mapped value is assigned one of six levels of danger, ranging from zero to five according to the following scale:

0 = baseline, no deviation
1 = minimum deviation
2 = mild deviation
3 = moderate deviation
4 = severe deviation
5 = very severe deviation In one particular embodiment, the equation used to transform the measured values of the parameters to the deviation indicators is of the following form:

$$y = \tfrac{1}{2}\{1 - \exp(-M(x - x_{bl})^2)\},$$

wherein y represents the value of the function, x represents the measured value of the parameter, $x_{bl}$ represents the baseline value for the parameter, and M represents the mapping parameter.

The mapping parameter, M, is determined by solving the above equation in terms of M. Accordingly, the mapping parameter is given by an equation of the form:

$$M = \frac{-\ln(1 - 2y)}{(x - x_{bl})^2}.$$

The mapping parameter, M, is then solved for two ranges of the parameter, x. The first range corresponds to values of x when $x < x_{bl}$ and the second range corresponds to values of x when $x \geq x_{bl}$. Alternatively, the first range corresponds to values of x when $x \leq x_{bl}$ and the second range corresponds to values of x when $x > x_{bl}$. Accordingly, the two values of the mapping parameter corresponding to the two ranges are given by the following equations:

$$M_{\min} = \frac{-\ln(1-2y')}{(x_{\min}-x_{bl})^2}$$

and $$M_{\max} = \frac{-\ln(1-2y'')}{(x_{\max}-x_{bl})^2}$$

wherein y' represents the value of the function at $x_{min}$, $x_{min}$ represents the minimum value of the parameter, y" represents the value of the function at $x_{max}$, and $x_{max}$ represents the maximum value of the parameter.

Once the values of the mapping parameter, M, for the two ranges have been determined, the mapped value of the parameter is generated using an equation of the form:

$$y = \frac{1}{2}\{1-\exp(-M_{min}(x-x_{bl})^2)\},$$

for $x < x_{bl}$ $$\frac{1}{2}\{1-\exp(-M_{max}(x-x_{bl})^2)\},$$

for $x \geq x_{bl}$

For each parameter, the measured value of the parameter, x, is plugged into the above equation, along with the appropriate baseline value, $x_{bl}$, and mapping parameter, M. Accordingly, a mapped value of each parameter, y, is generated.

The mapped value of each parameter, y, is then used to generate the deviation indicator for each parameter using an equation of the form:

$$DI = \lfloor K \times y \rfloor$$

wherein DI represents the deviation indicator, K represents a constant, y represents the value of the function, and "$\lfloor \ \rfloor$" represents a floor function that returns the largest integer value of an expression contained between the "$\lfloor$" and the "$\rfloor$" symbols.

Figure 5:
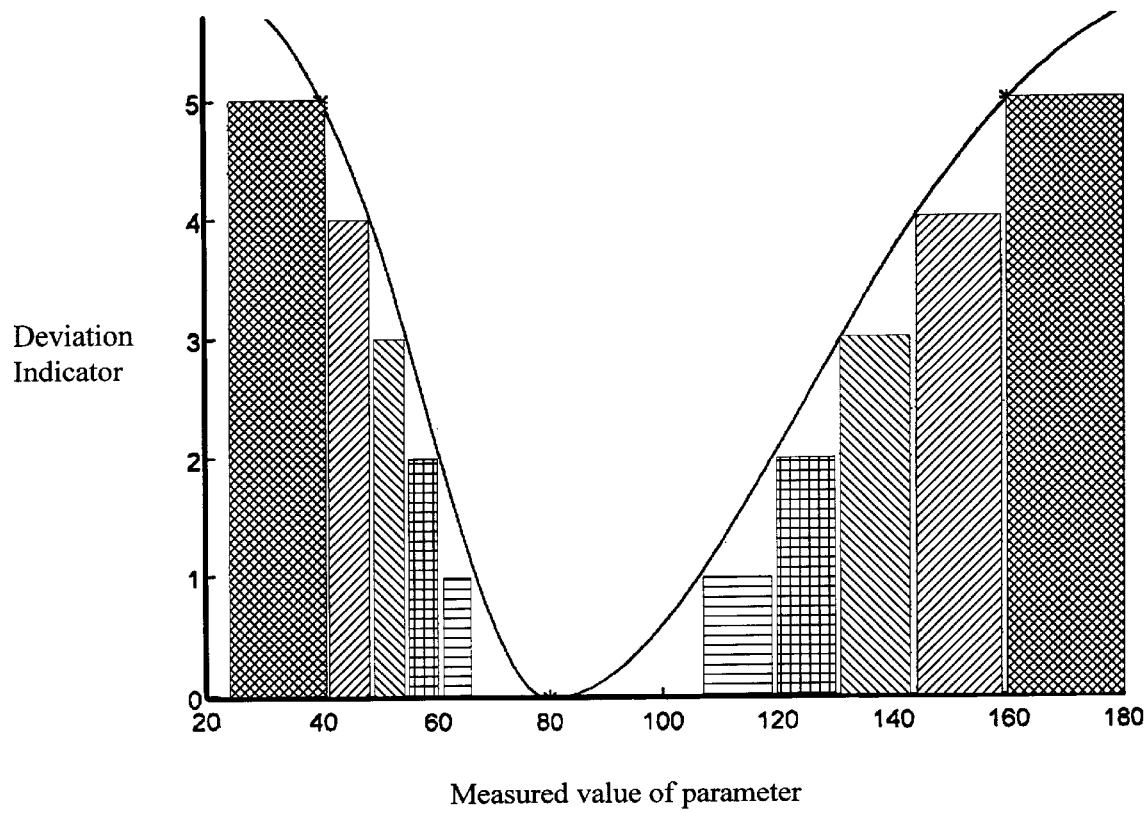
FIG. 5 is a graph showing a preferred function for transforming one measured parameter in accordance with the present invention.

A graph of a representative function for transforming the heart rate of a patient is shown in FIG. 5. When monitoring the heart rate of a human patient, a minimum of 40 BPM (beats per minute) and a maximum of 160 BPM is generally applicable. Although the baseline value of the heart rate will vary from patient to patient, a baseline value of 80 BPM could be considered normal for some patients. Accordingly, if we want to represent the deviation indicator one of six danger levels, we can assign the function at the minimum and maximum, y' and y", a value of 0.4 and the constant K a value of 12.5. As a result, $M_{min}$ is 0.001006 and $M_{max}$ is 0.000251. Therefore, if the heart rate is measured to be 60 BPM, the deviation indicator is determined to be 3. Similarly, if the heart rate is measured to be 100 BPM, the deviation indicator is determined to be 1. It is readily apparent from those values that the same magnitude shift results in a higher deviation indicator when the heart rate is lower than the baseline value than when the heart rate is higher than the baseline value.

Returning to FIG. 2, once the deviation indicators have been determined for each parameter, the deviation indicators are analyzed to generate one or more status indicators at step 61. The status indicators contain information about the overall status of the system.

Figure 4:
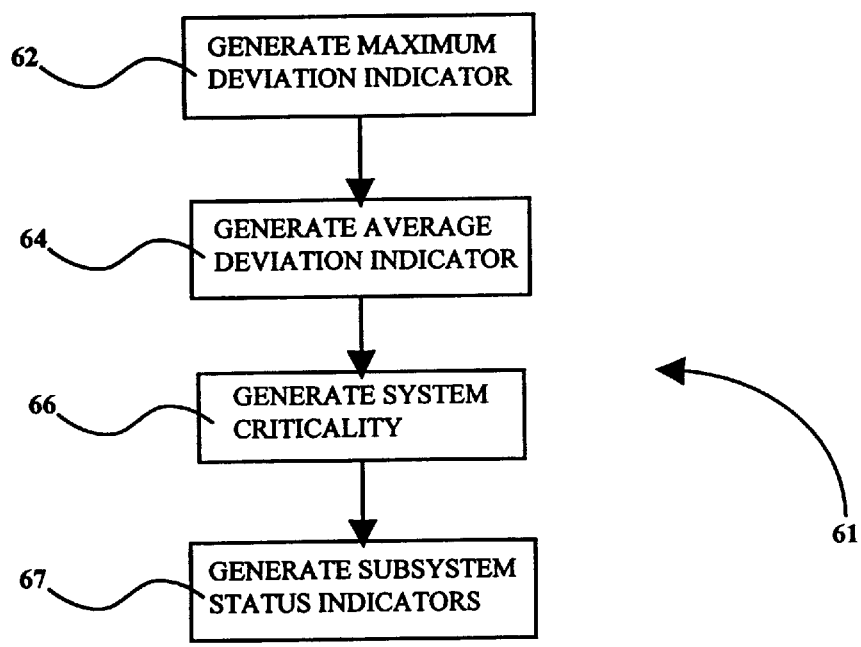
FIG. 4 is a flow chart showing the steps involved in an analysis step of FIG. 2.

The steps involved in generating the status indicators at step 61 are shown in more detail in FIG. 4. A maximum deviation indicator is determined at step 62 using an equation of the form:

$$DI_{max} = \max\{DI_i | i = 1, \ldots, n\}$$

wherein n is the total number of parameters being measured and max{ ... } is a function which returns the maximum value of the elements enclosed between the "{" and the "}".

In addition, an average deviation indicator is determined at step 64 using an equation of the form:

$$DI_{avg} = \frac{1}{n}\sum_{i=1}^{n} y_i$$

wherein $y_i$ is the mapped value of the $i^{th}$ parameter and n is the total number of parameters being measured.

Further, system criticality is determined at step 66 using an equation of the form:

$$DI_{cri} = \frac{n_m}{n}(DI_{max} - DI_{avg}) + DI_{avg}$$

wherein $n_m$ is the total number of parameters with a deviation indicator, DI, equal to $DI_{max}$.

In addition, one or more subsystems can be defined wherein the measured parameters are grouped according to subsystems. For a patient monitoring system, typical subsystems may include respiratory (RSP), central nervous system (CNS), and cardiovascular (CVS) subsystems. In some applications, the same parameter can be grouped in more than one subsystem. One or more subsystem status indicators associated with each subsystem are then generated at step 67 by analyzing the deviation indicators for the measured parameters which are grouped in each subsystem. The subsystem status indicators comprise the largest deviation indicator of all the parameters grouped in that subsystem. Alternatively, the subsystem status indicator can comprise the average of the deviation indicators for the parameters grouped in that subsystem. Also, the subsystem status indicator can comprise the subsystem criticality, which is determined in an analogous manner to the system criticality described above.

Figure 6:
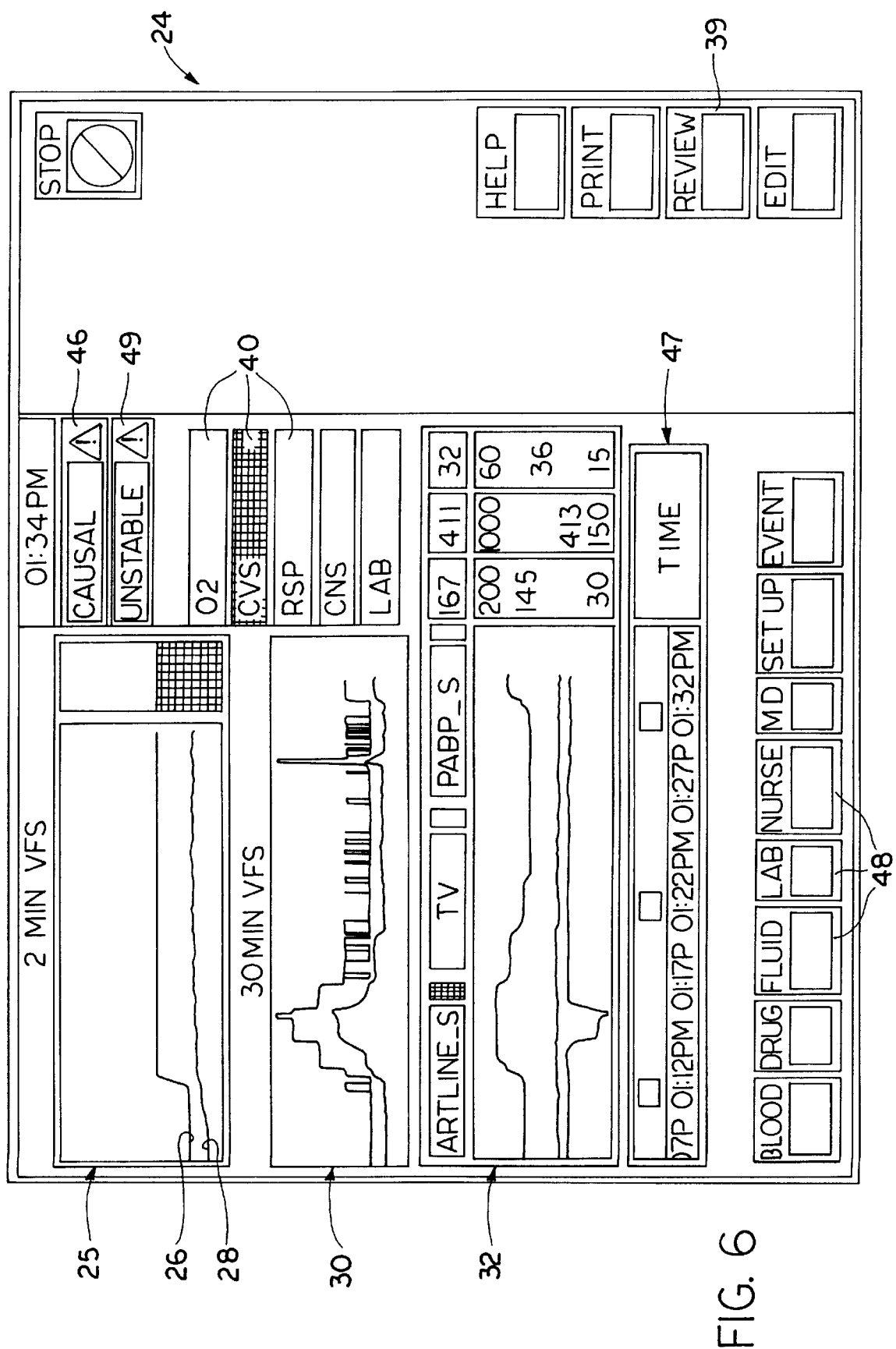
FIG. 6 is a view of a display in accordance with the present invention for monitoring a patient wherein the patient suffers from a mild cardiovascular (CVS) problem.
Figure 7:
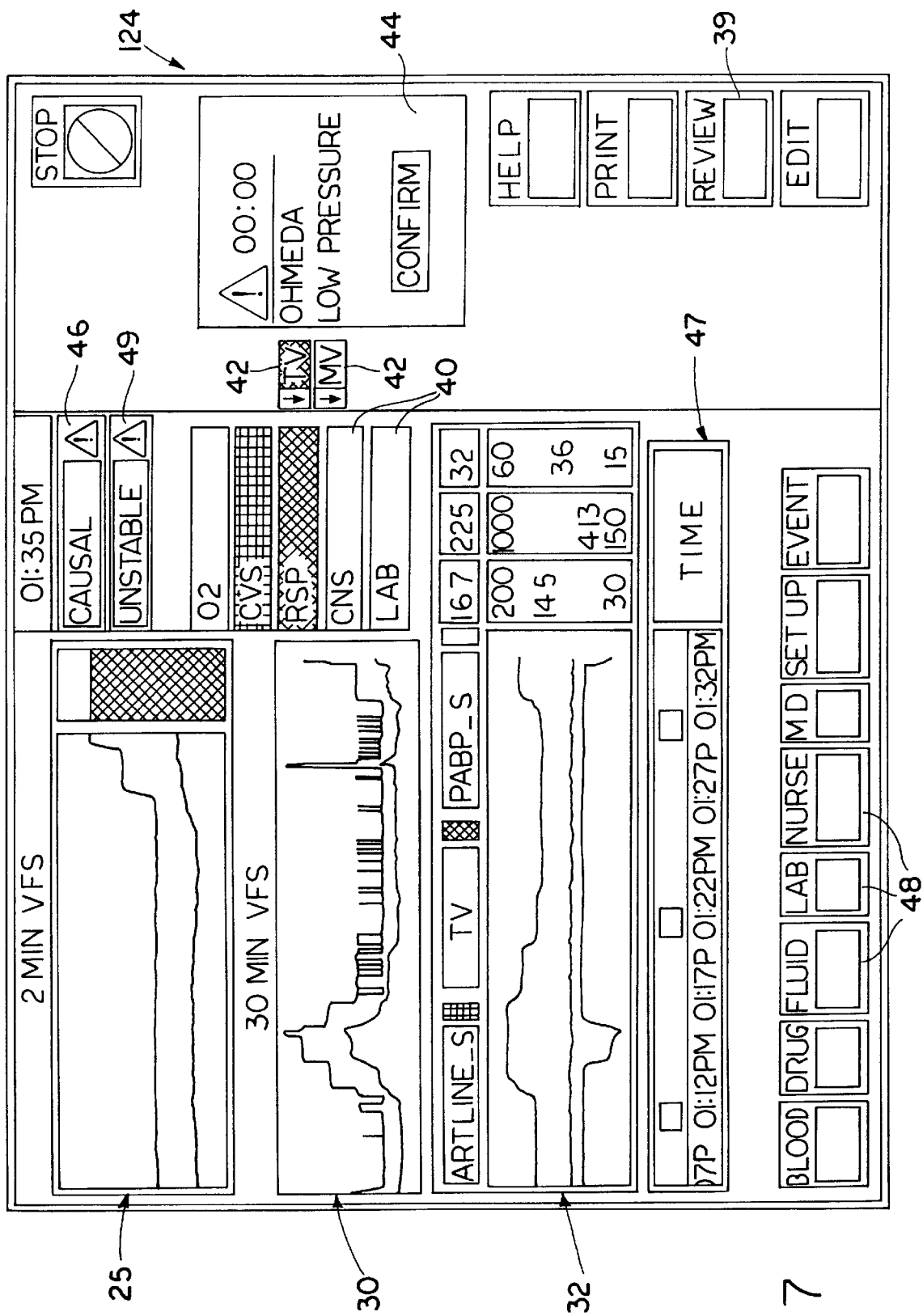
FIG. 7 is a view of the display in FIG. 6 wherein the patient suffers from a respiratory problem (RSP) caused mainly by a decrease of the tidal volume (TV), while the cardiovascular problem persists.
Figure 8:
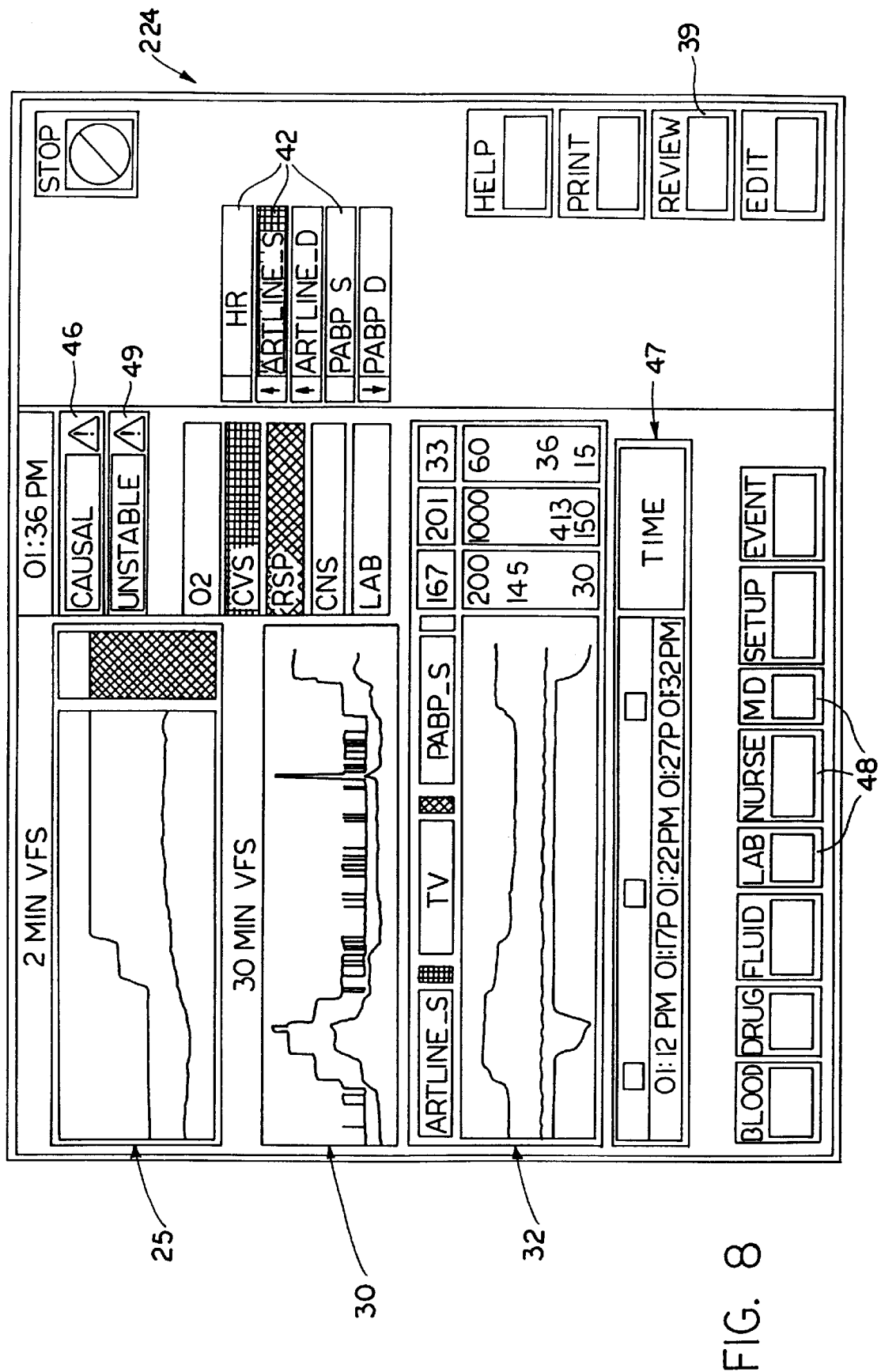
FIG. 8 is a view of the display in FIG. 7 wherein the patient suffers from an additional cardiovascular problem caused by an increase in systolic blood pressure, while the respiratory problem persists.

Returning to FIG. 2, after the status indicators have been generated at step 61, the status indicators are displayed in a display window 24 at step 68. An example of the display window 24 for displaying the status indicators is shown in FIGS. 6–8. The display window 24 in the figures is particularly designed for the medical monitoring of a patient. However, the display window 24 can be customized to adapt to the specific needs of the user and the type of system being monitored, such as the stock market. The display window 24 is preferably updated about once per second or faster. However, the display window 24 can be updated at any preselected time interval. Accordingly, the essentially continuous analysis helps detect and highlight even the most subtle changes before they become critical.

A short term display 25 established for a fixed period of time is provided for displaying a graph of the maximum deviation indicator and the average deviation indicator as a function of time. Preferably, the short term display 25 displays the value of the maximum and average deviation indicators over a specific or fixed time period. The short term display 25 preferably scrolls from right to left so that the fixed time period is always being displayed.

A long term display 30 that can be modified by the user is preferably provided. The long term display 30 is essentially identical to the short term display 25 except that the long term display 30 displays the values over a longer time period than the short term display and, as noted above, the time period displayed can be modified.

Figure 9:
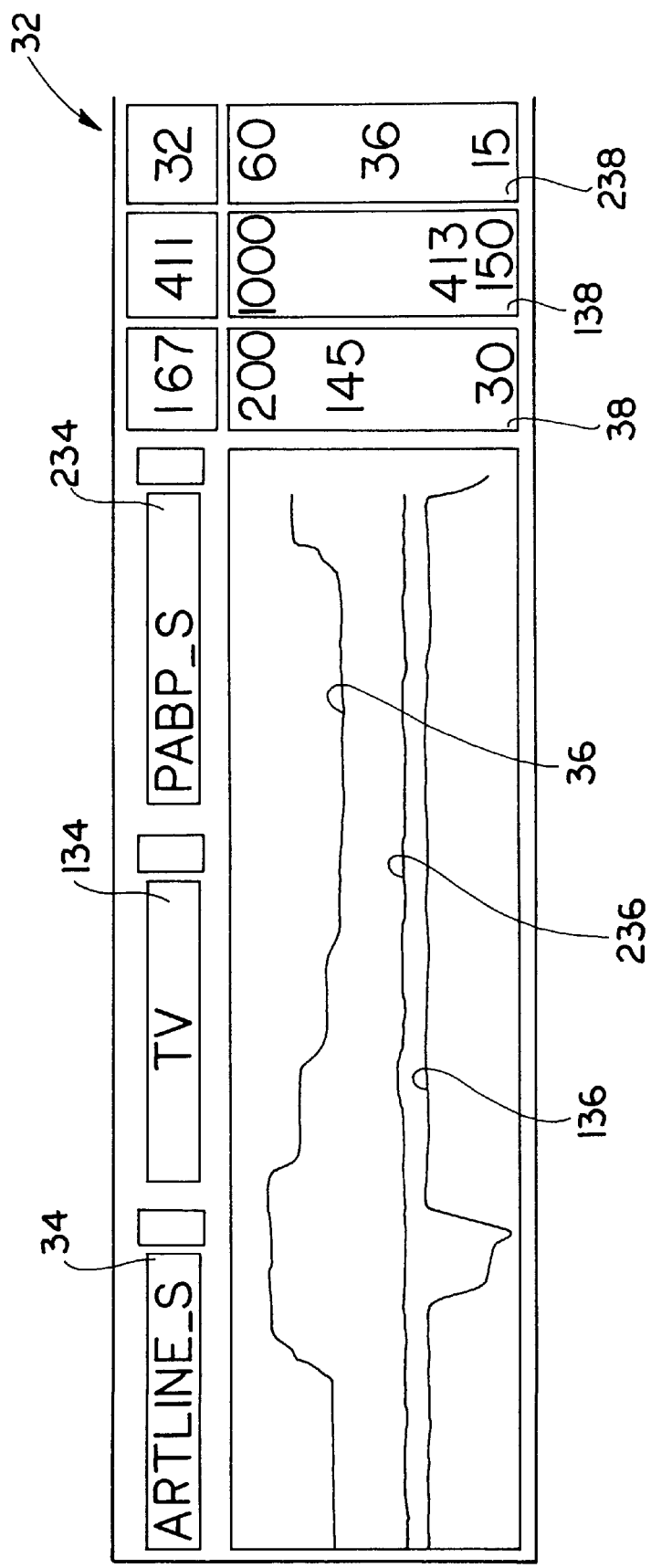
FIG. 9 is an expanded view of a parameter value display.

A parameter value display 32 can also be provided to display the measured value of one or more parameters as a function of time. The values of the parameters are plotted as a graph 36 of the value as a function of time. Preferably, the user is able to select which parameters are displayed. In the embodiment shown in FIGS. 6–9, the values for three different parameters are graphed, 36, 136, and 236, simultaneously on the same plot. The identity of the parameters being displayed are indicated by the parameter identifiers 34, 134, and 234. The parameter value display 32 also comprises parameter statistics indicators, 38, 138, and 238, which provide the current measured values and the baseline, minimum, and maximum values for each parameter being displayed. Color coding can be used to inform the user which graph 36 and parameter statistics indicator 38 corresponds to each parameter being graphed. Accordingly, as best shown in FIG. 9, the graph 36 and parameter statistics indicator 38 are preferably displayed in the same color as the parameter identifier 34. Similarly, graph 136 and indicator 138 are preferably displayed in the same color as identifier 134 and graph 236 and indicator 238 are preferably displayed in the same color as identifier 234.

The display window 24 can also comprise a subsystem alarm display 40. The subsystem alarm display 40 provides the user with important information regarding the parameters being measured. The subsystem alarm display 40 displays the subsystem status indicator which indicates the degree of deviation associated with each subsystem. Preferably, the degree of deviation is indicated by assigning different colors to the different degrees of deviation and displaying the subsystem alarm display 40 for each subsystem in the appropriate color. In one embodiment, the degrees of deviation are assigned colors ranging from white for no deviation to red for a very severe deviation. The intermediate degrees of deviation are assigned colors of varying shades of yellow and orange. In addition to the visual warning, an audio output can be provided to indicate the degree of deviation. In one embodiment, the audio output varies in pitch as the degree of deviation increases, thereby alerting the user.

In addition, the user can be given the option to view the particular parameters which contribute to the subsystem status indicator. As shown in FIGS. 7 and 8, the parameter deviation display 42 for the parameters which are contributing to the subsystem status indicator are displayed to the right of the subsystem status indicator. The color of the parameter deviation display 42 corresponds to the degree of deviation associated with the deviation indicator for that parameter. An up or down arrow is also displayed to indicate whether the measured value of the parameter has shifted above or below the baseline value for that parameter.

Figure 10:
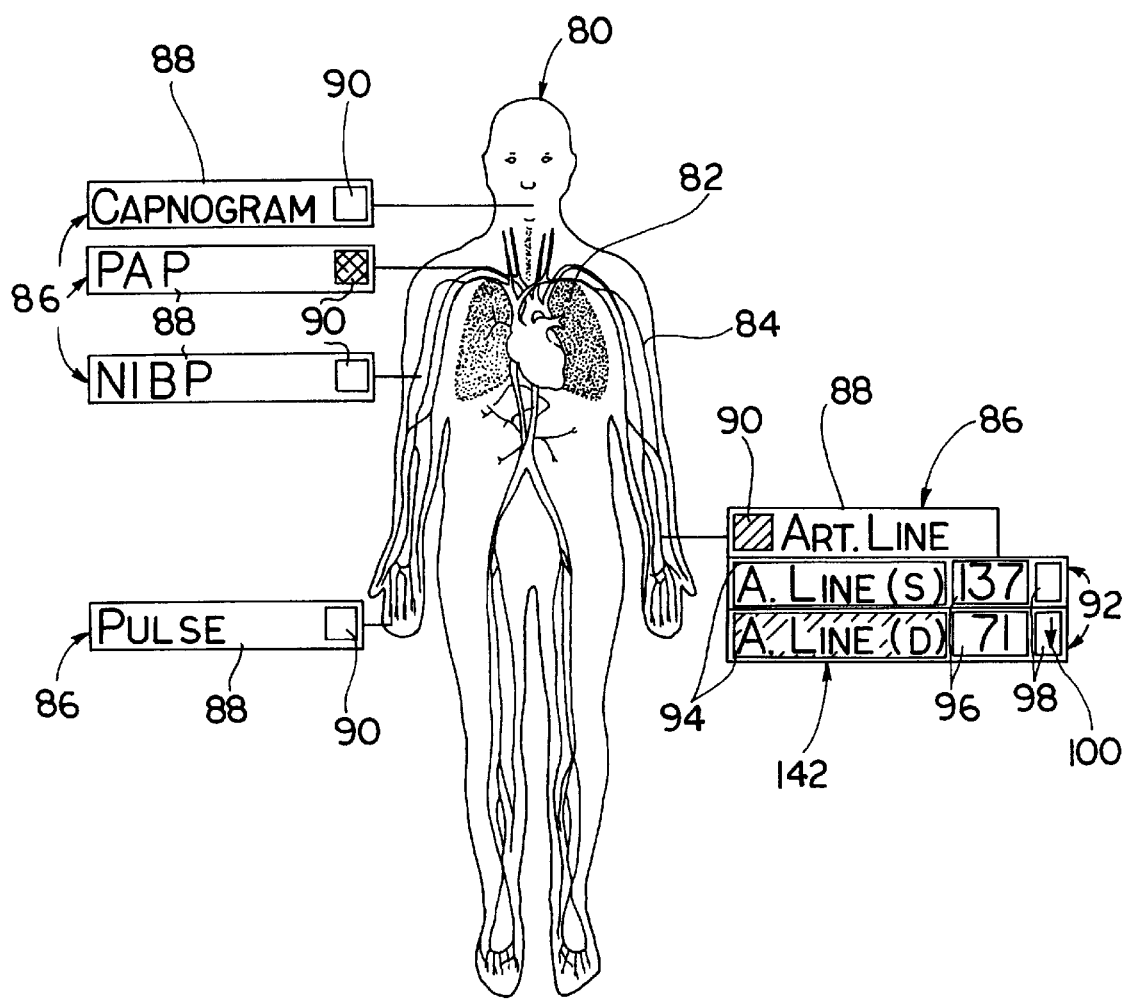
FIG. 10 is a view of a display in accordance with the present invention for showing the status of a patient being monitored.

The display window 24 may also comprise a pictorial representation of the general system for graphically displaying information about the system, as shown in FIG. 10. In that figure, the pictorial representation 80 is that of a human figure which is useful when the system being monitored is a human patient. The pictorial representation 80 shows structures, 82 and 84, representing the respiratory and circulatory subsystems respectively. A series of labels 86 are provided which identify the subsystems and/or sensors, as well as individual parameters associated with the system or data obtained from sensors. The labels 86 are also used for administration and management of inputs (i.e. blood) into patient and outputs (i.e. urine) from patient. In a preferred embodiment, the labels 86 are shown to illustrate certain parameters, namely capnogram, PAP, NIBP, pulse, and arterial line parameters of the respiratory and circulatory subsystems, but other subsystems, sensors and/or parameters can of course be used in place of the referenced subsystems, sensors and/or parameters. Each label 86 comprises a brief descriptor 88 which informs the user of the subsystem/sensor or parameter being identified by the label 86. The label 86 also comprises an indicator 90 for displaying the status of the subsystem/sensor or the parameter. When the label 86 identifies a subsystem and/or sensor, the indicator 90 displays the subsystem and/or sensor status indicator which indicates the degree of deviation associated with the subsystem and/or sensor. An up or down arrow may be displayed within indicator 90 to indicate whether the subsystem and/or sensor deviation indicator has shifted above or below the baseline value for that subsystem and/or sensor.

When the label 86 identifies a parameter associated with the general system, the indicator 90 displays the deviation indicator associated with that parameter. As previously described, the degree of deviation is preferably indicated by assigning different colors to the different degrees of deviation and displaying the indicator 90 in the appropriate color. An up or down arrow may be displayed within box 90 to indicate whether the parameter deviation indicator has shifted above or below the baseline value for that parameter.

When the label 86 identifies a subsystem and/or sensor, the user can be given the option to view the particular parameters which contribute to the status indicator of the subsystem and/or sensor. Accordingly, a parameter deviation display 142 for the parameters which are contributing to the subsystem and/or sensor status indicator can be displayed adjacent to the label 86 associated with the subsystem and/or sensor. As shown in FIG. 10, two parameters, the A. Line (s) and A. Line (d), contribute to the Art. Line sensor. Therefore, two display boxes 92 are provided corresponding to those two parameters. Each display box 92 comprises a descriptor 94 identifying the parameter, a measured value window 96 for displaying the measured value of the parameter, and a status window 98 indicating the degree of deviation associated with the deviation indicator for that parameter. The color of the descriptor 94 and the status window 98 may correspond to the degree of deviation associated with the deviation indicator for that parameter. An up or down arrow 100 may be displayed to indicate whether the deviation of the parameter has shifted above or below the baseline value for that parameter.

With regard to the subsystems, when the average deviation indicator for the subsystem illustrated in the pictorial representation 80 reaches a predetermined value, that subsystem is highlighted in the pictorial representation.

A sensor status display 44 can also be provided, as shown in FIG. 7. The sensor status display 44 indicates to the user either when a new sensor has started to function or when a sensor which was functioning ceases to function properly. The sensor status display 44 is particularly useful to alert the user that a sensor has been disconnected from the system.

A causal display 46 can also be provided. The casual display 46 is highlighted when a parameter changes from its baseline value to a predefined level or higher and remains at that level or higher for a minimum time. For example, the display 46 can be highlighted when the deviation indicator of a parameter changes from zero to two or higher and remains at a level of two or higher for more than about two minutes. The display 46 is highlighted by changing its color from a background color, such as grey, to a color which indicates a warning, such as orange. In one embodiment, when the causal display 46 is highlighted, information relating to the parameters which have contributed to the causal display 46 being highlighted appears in tabular form at the request of the user. Further, the indicator 46 preferably indicates the most recent event preceding the deviation.

The display window 24 may also comprise an unstable parameter display 49. The unstable parameter display 49 is highlighted whenever the sensors identify a parameter that deviates by two or more levels on the scale. The display 49 is highlighted by changing its color from a background color, such as grey, to a color which indicates a warning, such as orange. The display 49 remains highlighted as long as the parameter does not stabilize, i.e., continues to rise or fall on the scale.

Further, the display window 24 optionally comprises an event display 47. The event display 47 allows the user to record the occurrence of events so that the systems response to such events can be monitored. The occurrence of an event is recorded by the user by selecting the particular event which has occurred from an event selector 48. Preferably, the event selector 48 comprises a number of user selectable icons which are selected by clicking on the appropriate icon with a computer mouse. The occurrence of the event is then registered on the event display 47 indicating the time at which the event occurred.

The criticality indicator 45 combines both the average deviation of all the parameters being monitored and the number of parameters that contribute to the maximum deviation. This indicator 45 is displayed to the user upon request by selecting a time point from the time frame window or by selecting the criticality trend from a review utility 39.

The review utility 39 can be provided to allow the user to review the history status of the system at any selected time, from the time that the monitoring of the system began until the present time. In one embodiment, the review utility 39 is accessed by selecting an icon which appears on the display window 24 using a computer mouse.

Returning to FIG. 2, after the status indicators have been displayed at step 68, it is determined whether new values for the parameters are to be measured at step 70. If new values are to be measured, the method returns to step 52. However, if no new values are to be measured, the method proceeds to step 72, where the method stops.

The apparatus 10 and method of the present invention are useful in a wide range of applications. The ability of the user to monitor a plurality of parameters and identify problems at an early stage makes the invention particularly suited for examining patients in intensive care units, operating rooms, and emergency rooms; analyzing financial data associated with, for example, the stock market; monitoring parameters associated with control rooms, such as those used in industry, aviation, and power stations; and checking parameters associated with the automotive industry, in the manufacturing of cars and/or in the diagnosis of individual cars.

However, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for monitoring a system comprising:
    a. transformation means for transforming each value of a plurality of parameters associated with the system using a function dependent on at least baseline and critical values of the parameter;
    b. mapping means for mapping the function to a sequence of reference values and generating a deviation indicator for each parameter;
    c. analysis means for analyzing all of the deviation indicators and generating a single system status indicator; and
    d. a display means for displaying the system status indicator.

2. The apparatus as recited in claim 1 wherein the transformation means employs a function which exhibits a minimum sensitivity for deviations close to the baseline value of the parameter.

3. The apparatus as recited in claim 1 wherein the transformation means employs a sigmoid function.

4. The apparatus as recited in claim 1 wherein the display means comprises a pictorial representation of the system showing a structure associated with one of the parameters and a label identifying the structure, the label indicating a status of the parameter.

5. A method for monitoring a system comprising:
    a. a transformation step for transforming each value of a plurality of parameters associated with the system using a function dependent on at least baseline and critical values of the parameter, the function exhibiting a minimum sensitivity for deviations close to the baseline value of the parameter;
    b. a mapping step for mapping the function to a sequence of reference values and generating a deviation indicator for each parameter; and
    c. a display step for displaying the deviation indicator for at least one of the parameters.

6. The method as recited in claim 5 wherein the display step comprises a step of displaying a pictorial representation of the system showing a structure associated with one of the parameters and a label identifying the structure, the label indicating a status of the parameter.

7. A method for monitoring a system comprising:
    a. a transformation step for transforming each value of a plurality of parameters associated with the system using a function dependent on at least baseline and critical values of the parameter;
    b. a mapping step for mapping the function to a sequence of reference values and generating a deviation indicator for each parameter;
    c. an analysis step for analyzing all of the deviation indicators and generating a single system status indicator; and
    d. a display step for displaying the systems status indicator.

8. The method as recited in claim 7 wherein the transformation step employs a function which exhibits a minimum sensitivity for deviations close to the baseline value of the parameter.

9. The method as recited in claim 7 wherein the transformation step employs a sigmoid function.

10. The method as recited in claim 7 wherein the display step comprises a step of displaying a pictorial representation of the system showing a structure associated with one of the parameters and a label identifying the structure, the label indicating a status of the parameter.

11. The method as recited in claim 7 wherein the analysis step comprises the steps of:
   a. defining at least one subsystem; and
   b. generating a single average deviation indicator for each subsystem.

12. The method as recited in claim 11 further comprising a second display step for displaying the average deviation indicator for each subsystem.

13. The method as recited in claim 12 wherein the second display step comprises a step of displaying a pictorial representation of the system showing a structure associated with one of the subsystems and a label identifying the structure, the label indicating a status of the subsystem.

14. A method for monitoring a system comprising:
   a. a transformation step for transforming each value of a sensor associated with the system using a function dependent on at least baseline and critical values of the sensor;
   b. a mapping step for mapping the function to a sequence of reference values and generating a deviation indicator for each sensor;
   c. an analysis step for analyzing all of the deviation indicators and generating a single system status indicator; and
   d. a display step for displaying the system status indicator.

15. The method as recited in claim 14 wherein the analysis step comprises the steps of:
   a. defining at least one sensor; and
   b. generating a single average deviation indicator for each sensor.

16. The method as recited in claim 15 further comprising a second display step for displaying the average deviation indicator for each sensor.

17. The method as recited in claim 16 wherein the second display step comprises a step of displaying a pictorial representation of the system showing a structure associated with one of the sensors and a label identifying the structure, the label indicating a status of the sensor.

18. An apparatus for monitoring a system comprising:
   a. transformation means for transforming each value of a plurality of parameters associated with the system using a function dependent on at least baseline and critical values of the parameter;
   b. mapping means for mapping the function to a sequence of reference values and generating a deviation indicator for each parameter; and
   c. analysis means for analyzing all of the deviation indicators and generating a single average deviation indicator.

19. The apparatus as recited in claim 18 wherein the transformation means employs a function which exhibits a minimum sensitivity for deviations close to the baseline value of the parameter.

20. The apparatus as recited in claim 18 further comprising a plurality of sensors operative to measure the values of the parameters.

21. The apparatus as recited in claim 18 further comprising a display means for displaying the average deviation indicator.

22. An apparatus for monitoring a system comprising:
   a. transformation means for transforming each value of a plurality of parameters associated with the system using a function dependent on at least baseline and critical values of the parameter;
   b. mapping means for mapping the function to a sequence of reference values and generating a deviation indicator for each parameter; and
   c. analysis means for analyzing all of the deviation indicators and generating a single system criticality indicator.

23. The apparatus as recited in claim 22 wherein the transformation means employs a function which exhibits a minimum sensitivity for deviations close to the baseline value of the parameter.

24. The apparatus as recited in claim 22 further comprising a plurality of sensors operative to measure the values of the parameters.

25. The apparatus as recited in claim 22 further comprising a display means for displaying the system criticality indicator.

26. An apparatus for monitoring a patient comprising:
   a. transformation means for transforming each value of a plurality of medical parameters associated with the patient using a function dependent on at least baseline and critical values of the medical parameter;
   b. mapping means for mapping the function to a sequence of reference values and generating a deviation indicator for each medical parameter; and
   c. analysis means for analyzing all of the deviation indicators and generating a single average deviation indicator.

27. An apparatus for monitoring a patient comprising:
   a. transformation means for transforming each value of a plurality of medical parameters associated with the patient using a function dependent on at least baseline and critical values of the medical parameter;
   b. mapping means for mapping the function to a sequence of reference values and generating a deviation indicator for each medical parameter; and
   c. analysis means for analyzing all of the deviation indicators and generating a single patient criticality indicator.

28. A method for monitoring a system comprising:
   a. a transformation step for transforming each value of a plurality of parameters associated with the system using a function dependent on at least baseline and critical values of the parameter;
   b. a mapping step for mapping the function to a sequence of reference values and generating a deviation indicator for each parameter; and
   c. an analysis step for analyzing all of the deviation indicators and generating a single average deviation indicator.

29. The method as recited in claim 28 wherein the transformation step employs a function which exhibits a minimum sensitivity for deviations close to the baseline value of the parameter.

30. The method as recited in claim 28 further comprising a step of displaying the average deviation indicator.

31. The method as recited in claim 28 wherein the analysis step comprises the steps of:
   a. defining at least one subsystem; and
   b. generating an average deviation indicator for each subsystem.

32. A method for monitoring a system comprising:
   a. a transformation step for transforming each value of a plurality of parameters associated with the system using a function dependent on at least baseline and critical values of the parameter;
   b. a mapping step for mapping the function to a sequence of reference values and generating a deviation indicator for each parameter; and c. an analysis step for analyzing all of the deviation indicators and generating a single criticality indicator.

33. The method as recited in claim 32 wherein the transformation step employs a function which exhibits a minimum sensitivity for deviations close to the baseline value of the parameter.

34. The method as recited in claim 32 wherein the transformation step employs a sigmoid function.

35. The method as recited in claim 32 further comprising a step of displaying the system criticality indicator.

36. The method as recited in claim 32 wherein the analysis step comprises the steps of:

a. defining at least one subsystem; and
   b. generating a criticality indicator for each subsystem.

37. A method for monitoring a patient comprising:

a. a transformation step for transforming each value of a plurality of medical parameters associated with the patient using a function dependent on at least baseline and critical values of the medical parameter, the function exhibiting a minimum sensitivity for deviations close to the baseline value of the parameter;

b. a mapping step for mapping the function to a sequence of reference values and generating a deviation indicator for each medical parameter; and c. an analysis step for analyzing all of the deviation indicators and generating a single average deviation indicator.

38. A method for monitoring a patient comprising:

a. a transformation step for transforming each value of a plurality of medical parameters associated with the patient using a function dependent on at least baseline and critical values of the medical parameter;

b. a mapping step for mapping the function to a sequence of reference values and generating a deviation indicator for each medical parameter; and c. an analysis step for analyzing all of the deviation indicators and generating a single patient criticality indicator.

* * * * *